(12) United States Patent
Yamagawa et al.

(10) Patent No.: US 9,512,280 B2
(45) Date of Patent: Dec. 6, 2016

(54) ORGANIC/INORGANIC COMPOSITE, MANUFACTURING METHOD THEREFOR, DENTAL MATERIAL, AND BONE SUBSTITUTE MATERIAL

(71) Applicants: TOKUYAMA DENTAL CORPORATION, Tokyo (JP); NATIONAL INSTITUTE OF ADVANCED INDUSTRIALSCIENCE AND TECHNOLOGY, Tokyo (JP)

(72) Inventors: Jun-ichiro Yamagawa, Tokyo (JP); Hiroshi Shimizu, Tokyo (JP); Yongjin Li, Tokyo (JP)

(73) Assignees: TOKUYAMA DENTAL CORPORATION, Tokyo (JP); NATIONAL IINSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 104 days.

(21) Appl. No.: 14/364,108

(22) PCT Filed: Nov. 20, 2012

(86) PCT No.: PCT/JP2012/080065
§ 371 (c)(1),
(2) Date: Jun. 10, 2014

(87) PCT Pub. No.: WO2013/088921
PCT Pub. Date: Jun. 20, 2013

(65) Prior Publication Data
US 2015/0011673 A1 Jan. 8, 2015

(30) Foreign Application Priority Data
Dec. 15, 2011 (JP) .................. 2011274735

(51) Int. Cl.
| | | |
|---|---|---|
| *A61K 6/08* | (2006.01) | |
| *C08J 3/20* | (2006.01) | |
| *A61K 6/087* | (2006.01) | |
| *A61L 27/44* | (2006.01) | |
| *C08K 3/22* | (2006.01) | |
| *C08K 3/36* | (2006.01) | |
| *C08L 71/00* | (2006.01) | |
| *C08G 65/40* | (2006.01) | |
| *A61K 6/00* | (2006.01) | |

(52) U.S. Cl.
CPC ............... *C08J 3/203* (2013.01); *A61K 6/087* (2013.01); *A61L 27/446* (2013.01); *C08G 65/4012* (2013.01); *C08K 3/22* (2013.01); *C08K 3/36* (2013.01); *C08L 71/00* (2013.01); *A61K 6/0008* (2013.01); *C08G 2650/40* (2013.01); *C08J 2371/00* (2013.01); *C08K 2003/2241* (2013.01)

(58) Field of Classification Search
CPC .................................................... A61K 6/0008
See application file for complete search history.

(56) References Cited

U.S. PATENT DOCUMENTS

| | | | |
|---|---|---|---|
| 2002/0115742 A1 | 8/2002 | Trieu | |
| 2007/0015110 A1* | 1/2007 | Zhang | A61C 8/0012 433/173 |
| 2008/0318318 A1 | 12/2008 | Shimizu | |
| 2009/0301346 A1 | 12/2009 | Tanaka | |
| 2011/0196062 A1 | 8/2011 | Craig | |

FOREIGN PATENT DOCUMENTS

| | | |
|---|---|---|
| JP | 1149929 A | 2/1999 |
| JP | 1180547 A | 3/1999 |
| JP | 2004521685 A | 7/2004 |
| JP | 2004256592 A | 9/2004 |
| JP | 2007138338 A | 6/2007 |
| JP | 2008260720 A | 10/2008 |
| JP | 2008541874 A | 11/2008 |
| JP | 2009029114 A | 2/2009 |
| JP | 2010244932 A | 10/2010 |
| WO | 2008068862 A1 | 6/2008 |
| WO | 2010045105 A1 | 4/2010 |

OTHER PUBLICATIONS

Extended European Search corresponding to Application No. 12858186.5-1306/2792712 PCT/JP2012/080065; Date of Issuance: Sep. 14, 2015.
International Search Report for international application No. PCT/JP2012/080065, mailed on Jan. 22, 2013. English translation attached.
Japanese Notice of Reasons for Rejection corresponding to Application No. 2012-256019: Mailing Date: Sep. 6, 2016, with English translation.

* cited by examiner

*Primary Examiner* — Michael Pepitone
(74) *Attorney, Agent, or Firm* — CANTOR COLBURN LLP

(57) ABSTRACT

Provided are: an organic/inorganic composite, and a manufacturing method therefor; and a dental material and bone substitute material manufactured using the organic/inorganic composite. The organic/inorganic composite includes: (A) 100 parts by mass of a thermoplastic resin containing as a main component at least one kind selected from a polyarylketone resin and a polysulfone resin; and (B) 60 to 300 parts by mass of an inorganic particle mixture dispersed in the thermoplastic resin, in which the inorganic particle mixture contains inorganic particles each having a particle diameter of from 200 to 700 nm at a content of 25 vol % or more, and inorganic particles each having a particle diameter of from 40 to 100 nm at a content of 10 vol % or more.

19 Claims, 2 Drawing Sheets

ORGANIC/INORGANIC COMPOSITE, MANUFACTURING METHOD THEREFOR, DENTAL MATERIAL, AND BONE SUBSTITUTE MATERIAL

CROSS REFERENCE TO RELATED APPLICATIONS

This is the U.S. national stage of application No. PCT/JP2012/080065, filed on 20 Nov. 2012. Priority under 35 U.S.C. §119(a) and 35 U.S.C. §365(b) is claimed from Japanese Application No. 2011-274735, filed 15 Dec. 2011, the disclosure of which is also incorporated herein by reference.

TECHNICAL FIELD

The present invention relates to an organic/inorganic composite, a manufacturing method therefor, a dental material, and a bone substitute material.

BACKGROUND ART

A significant reduction in cost can be achieved by substituting a metal part with a molded article of a reinforced resin material. Accordingly, active studies on substitution have been performed (see, for example, Patent Literature 1 and Patent Literature 2).

The resin material to be used as described above has advantages such as (1) a reduction in weight, (2) an improvement in electrical insulation, and (3) an improvement in chemical resistance. Accordingly, applications of the resin material have expanded into substitute materials for various metal parts, and its amount of use has been increasing. In addition, particularly in the field of medical materials, a metal material such as titanium has been used as a material for implantation such as an artificial bone, an artificial joint, or an artificial tooth root. In recent years, however, the resin material has been utilized also in such field.

However, as compared to a metal, the resin material generally has problems such as having a large linear coefficient of expansion, having a low heat-resistant temperature and mechanical strength, being liable to deform or decompose, being liable to dissolve in an organic solvent, and being liable to expand by water absorption. Therefore, it is not easy to substitute a metal part with a resin part.

To solve the above-mentioned problems, there have been proposed synthetic resin products having various functions enhanced in accordance with intended applications by selecting a resin having high heat resistance such as an engineering plastic or a super engineering plastic. Further, there is also a proposal of a composite material having inorganic particles blended therein as a filler.

CITATION LIST

Patent Literature

[PTL 1] JP 11-49929 A (Scope of Claims)
[PTL 2] JP 11-80547 A (Scope of Claims)

SUMMARY OF INVENTION

Technical Problem

However, it is not easy to fill a resin having a high melting temperature such as a super engineering plastic with inorganic particles at a high rate. First, the inorganic particles have a large bulk volume as compared to a resin raw material, and hence when mixed with resin pellets, the inorganic particles are difficult to conform well to a molten resin. Accordingly, failure in the dispersion of the inorganic particles in the resin, such as clumping of the inorganic particles, is liable to occur. Such phenomenon is particularly remarkable in the case where the inorganic particles have small particle diameters, or in the case where the blending amount of the inorganic particles is increased. In addition, as the amount of the inorganic particles added to the resin in a molten state is increased, the melt viscosity of the resin mixture remarkably increases, and hence the inorganic particles and the molten resin cannot be uniformly kneaded. Accordingly, failure in the dispersion of the inorganic particles in the resin, such as clumping of the inorganic particles, occurs, and moreover, a local temperature increase may be caused, resulting in the occurrence of the problem of a burnt resin in some cases. To solve such problems, it is possible to decrease the melt viscosity by setting a high apparatus temperature. However, this causes a problem such as the promotion of pyrolysis due to the exposure of the resin to high temperature. Against such background, investigation of the characteristics of the obtained composite material has revealed that a satisfactory product has not necessarily been able to be obtained heretofore.

The present invention has been made in order to solve the problems as described above. An object of the present invention is to provide: an organic/inorganic composite having inorganic particles blended in a resin having a high melt viscosity at a high filling rate and with high dispersibility, the organic/inorganic composite having high mechanical strength, and a manufacturing method therefor; and a dental material and bone substitute material manufactured using the organic/inorganic composite.

Solution to Problem

The inventors of the present invention have made intensive studies in order to overcome the above-mentioned problems. As a result, the inventors have found that an organic/inorganic composite body having extremely high mechanical strength is obtained by mixing a resin having a high melting temperature with inorganic particles having different specific particle diameters, and mixing the highly dispersed inorganic particles as a filling material at a specific mixing ratio. Thus, the present invention has been accomplished.

That is, an organic/inorganic composite of the present invention includes: (A) 100 parts by mass of a thermoplastic resin containing as a main component at least one kind selected from a polyarylketone resin and a polysulfone resin; and (B) 60 to 300 parts by mass of an inorganic particle mixture dispersed in the thermoplastic resin, in which the inorganic particle mixture contains inorganic particles each having a particle diameter of from 200 to 700 nm at a content of 25 vol % or more, and inorganic particles each having a particle diameter of from 40 to 100 nm at a content of 10 vol % or more.

In an organic/inorganic composite according to one embodiment of the present invention, (B) the inorganic particle mixture preferably further contains inorganic particles each having a particle diameter of from 1 to 10 μm at a content of from 10 to 55 vol %.

In an organic/inorganic composite according to another embodiment of the present invention, the inorganic particles constituting (B) the inorganic particle mixture preferably include silica-based inorganic particles.

An organic/inorganic composite according to another embodiment of the present invention, the inorganic particles preferably include titanium dioxide-based particles.

An organic/inorganic composite according to another embodiment of the present invention, (A) the resin preferably includes polyether ether ketone.

An organic/inorganic composite according to another embodiment of the present invention, the organic/inorganic composite preferably has a bending strength of 200 MPa or more, a modulus of elasticity of 6 GPa or more, and a fracture energy of 5 N/mm or more.

A manufacturing method for an organic/inorganic composite according to a first embodiment of the present invention includes melt-kneading raw materials including (A) 100 parts by mass of a thermoplastic resin containing as a main component at least one kind selected from a polyarylketone resin and a polysulfone resin, and (B) 60 to 300 parts by mass of an inorganic particle mixture containing inorganic particles each having a particle diameter of from 200 to 700 nm at a content of 25 mass % or more, and inorganic particles each having a particle diameter of from 40 to 100 nm at a content of 10 mass % or more, by applying a shear flow field and an elongation field.

A manufacturing method for an organic/inorganic composite according to a second embodiment of the present invention includes: supplying raw materials including (A) 100 parts by mass of a thermoplastic resin containing as a main component at least one kind selected from a polyarylketone resin and a polysulfone resin, and (B) 60 to 300 parts by mass of an inorganic particle mixture containing inorganic particles each having a particle diameter of from 200 to 700 nm at a content of 25 mass % or more, and inorganic particles each having a particle diameter of from 40 to 100 nm at a content of 10 mass % or more, to a melt-kneading apparatus including an internal-return screw that transfers a melt-kneaded product of the raw materials, which is transferred to a screw forward end, back to a rear end; and melt-kneading the raw materials under heating at from 200 to 500° C. under conditions of a rotation number of the screw of from 300 to 3,000 rpm and a shear rate of from 450 to 4,500 $sec^{-1}$ by circulating the raw materials for a given period of time.

In a manufacturing method for an organic/inorganic composite according to another embodiment mode of the first and second embodiments of the present invention, (B) the inorganic particle mixture preferably includes inorganic particles surface-treated with a surface treatment agent containing a (meth)acrylic group.

In a manufacturing method for an organic/inorganic composite according to another embodiment mode of the first and second embodiments of the present invention, the inorganic particles surface-treated with a surface treatment agent containing a (meth)acrylic group preferably include inorganic particles surface-treated with a surface treatment agent represented by the following formula (1):

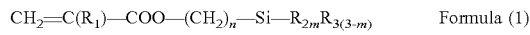

$$CH_2=C(R_1)-COO-(CH_2)_n-Si-R_{2m}R_{3(3-m)} \quad \text{Formula (1)}$$

(in the formula (1), $R_1$ represents a hydrogen atom or a methyl group, $R_2$ represents an alkoxy group having 1 to 6 carbon atoms, an isocyanate group, or a chlorine atom, $R_3$ represents a hydrocarbon group having 1 to 6 carbon atoms, m represents 1, 2, or 3, and n represents an integer of from 3 to 20).

A dental material of the present invention includes the organic/inorganic composite of the present invention.

A bone substitute material of the present invention includes the organic/inorganic composite of the present invention.

Advantageous Effects of Invention

According to one embodiment of the present invention, it is possible to provide: the organic/inorganic composite having inorganic particles blended in a resin having a high melt viscosity at a high filling rate and with high dispersibility, the organic/inorganic composite having high mechanical strength, and the manufacturing method therefor; and the dental material and bone substitute material manufactured using the organic/inorganic composite.

DESCRIPTION OF EMBODIMENTS

Figure 1:
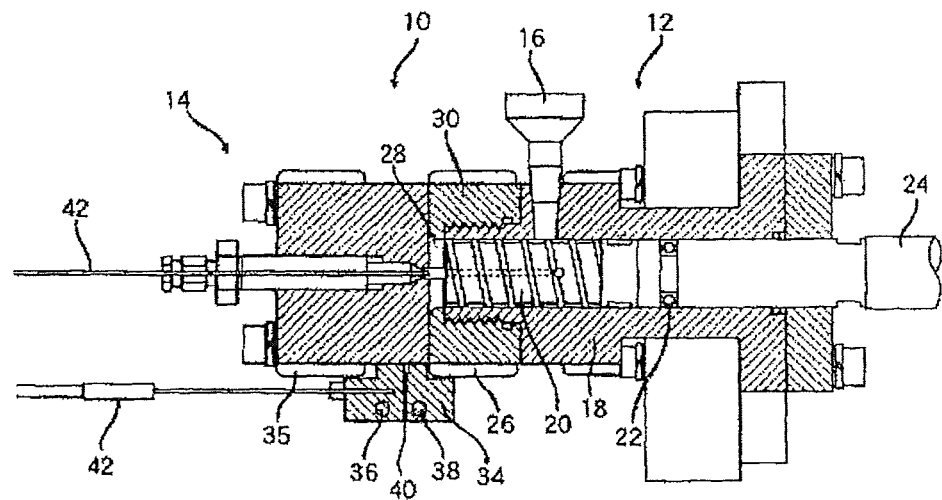
FIG. 1 is an overall view of an example of an apparatus for manufacturing an organic/inorganic composite having mixed inorganic particles uniformly dispersed in (A) a thermoplastic resin containing as a main component at least one kind selected from a polyarylketone resin and a polysulfone resin.

Hereinafter, an organic/inorganic composite according to a preferred embodiment of the present invention is described. However, the present invention is by no means limited to the embodiment described below.

(Organic/Inorganic Composite)

An organic/inorganic composite according to this embodiment includes: (A) 100 parts by mass of a thermoplastic resin containing as a main component at least one kind selected from a polyarylketone resin and a polysulfone resin (hereinafter referred to as "resin raw material"); and (B) 60 to 300 parts by mass of an inorganic particle mixture dispersed in the thermoplastic resin, in which the inorganic particle mixture contains inorganic particles each having a particle diameter of from 200 to 700 nm at a content of 25 vol % or more, and inorganic particles each having a particle diameter of from 40 to 100 nm at a content of 10 vol % or more. It should be noted that the main component means that the content of (A) the polyarylketone resin and/or the polysulfone resin contained in 100 parts by mass of the resin raw material is 70 parts by mass or more. In particular, it is more preferred that the content of (A) the polyarylketone resin and/or the polysulfone resin contained in 100 parts by mass of the resin raw material be 95 parts by mass or more.

In the organic/inorganic composite according to this embodiment, through the use of the inorganic particle mixture constructed with a combination of particle sizes in different specific ranges and a specific blending ratio with respect to the resin raw material, the inorganic particle mixture can be uniformly dispersed in the resin raw material, and its filling rate and mechanical strengths, i.e., bending strength, modulus of elasticity, and fracture energy can be further improved.

Herein, the bending strength refers to the maximum stress applied to a test object in a stress-strain curve obtained when a three-point bending test is performed. As its value becomes larger, the test object can endure a higher load (loading).

The modulus of elasticity refers to a constant of proportionality between stress and strain in a stress-strain curve obtained when a three-point bending test is performed, and has the same meaning as bending modulus of elasticity. As its value becomes larger, the test object is less liable to deform, and can maintain the shape of the original structure with respect to a stress. A general resin material has a modulus of elasticity of from about 2 to 3 GPa, while a biological hard tissue such as bone is said to have a modulus of elasticity of from about 10 to 20 GPa. Accordingly, when the resin material is used as it is as a dental material or a bone substitute material, problems such as fracture due to stress concentration and biological tissue absorption occur owing to significant differences in dynamic properties, and thus the resin material has poor biocompatibility. However, the organic/inorganic composite according to this embodiment has a higher modulus of elasticity than the general resin material and more similar properties to those of the biological hard tissue, and hence is particularly excellent.

The fracture energy refers to energy required for fracture in a stress-strain curve obtained when a three-point bending test is performed, and can be determined by the integrated value of stress and strain. As its value becomes larger, the test object is less liable to fracture. In general, as a resin is blended with an increasing amount of inorganic particles, there is such a tendency that the modulus of elasticity improves, the organic/inorganic composite body becomes brittle, and the fracture energy lowers. Meanwhile, the organic/inorganic composite body according to this embodiment has a feature of exhibiting high fracture energy while having a high modulus of elasticity, that is, being ameliorated in brittleness, and hence hardly undergoes the occurrence of a crack and breakage.

Next, details of (A) the resin raw material and (B) the inorganic particle mixture contained in the organic/inorganic composite according to this embodiment of the present invention are described.

(A) Resin Raw Material

The resin raw material constituting the organic/inorganic composite according to this embodiment contains (A) at least one kind selected from the polyarylketone resin and the polysulfone resin.

The polyarylketone resin is a thermoplastic resin having in a structural unit thereof an aromatic nucleus bond, an ether bond, and a ketone bond, and in most cases, has a linear polymer structure in which benzene rings are bonded to each other through an ether and a ketone. Typical examples thereof include polyetherketone (PEK), polyetheretherketone (PEEK), polyetherketoneketone (PEKK), and polyetherketoneetherketone ketone (PEKEKK). In addition, the resin may contain a biphenyl structure, a sulfonyl group, or any other copolymerizable monomer unit without departing from the gist of the present invention. These polyarylketone resins each have a high value for its melting temperature, i.e., from 300 to 450° C. Herein, the melting temperature refers to a temperature at which the resin shows such fluidity that its melt-kneading with the inorganic particles becomes possible, and in the case of a crystalline resin having a melting point, is selected from a temperature region higher than the melting point and lower than a pyrolysis temperature. In addition, in the case of an amorphous resin having no definite melting point, the melting temperature is selected from a temperature region higher than a glass transition temperature and lower than the pyrolysis temperature. It should be noted that the melting point and glass transition temperature of the resin can be found from differential scanning calorimetry results, and the pyrolysis temperature can be found from thermogravimetry results.

In this embodiment, polyetheretherketone in which linkages are repeatedly arranged in the following order is preferably used: an ether, an ether, and a ketone. The polyetheretherketone having the repeating unit is commercially available under the trade name, for example, "PEEK". Specific examples thereof include VESTAKEEP (Daicel-Evonik Ltd.) and VICTREX PEEK (VICTREX). It should be noted that one kind of the polyarylketone resins may be used alone, or two or more kinds thereof may be used in combination. As a grade to be used as the resin raw material according to this embodiment, an arbitrary one may be used, and one having physical properties (such as melt viscosity) in accordance with purposes may be selected. A natural grade containing no other component is preferably used. Among natural grades, a high-fluidity grade having a low melt viscosity and high fluidity, which facilitates molding such as injection molding, is preferably used, and its melt viscosity at 400° C. is preferably less than 200 Pa·s as measured by a method in conformity with the method of ISO 11443. Specific examples thereof include VICTREX PEEK 90G (100 Pa·s) and VESTAKEEP 1000G (150 Pa.). Each of them has a melting point of 334° C., and a preferred melting temperature therefor is from 360 to 400° C. In general, when a resin molded body is obtained with a natural grade alone, any of grades ranging from a medium viscosity grade (e.g., VICTREX PEEK 381G: melt viscosity of 300 Pa·s) to a high viscosity grade (e.g., VICTREX PEEK 450G: melt viscosity of 350 Pa·s) each having high durability is selected. In contrast, in the case of producing an organic/inorganic composite material like that of the present invention, a synergetic effect by the blending of the inorganic particles allows a high fluidity grade to be preferably used from the viewpoint of high mechanical strength.

The polysulfone resin (PSF) is an amorphous thermoplastic resin containing in its constituent molecule a sulfonyl group, and in many cases, contains an aromatic ring to achieve high functionality. A polyether sulfone resin (PES) and a polyphenylsulfone resin (PPSU) are also included in the polysulfone resin as sulfonyl group-containing resins. These polysulfone resins also each generally have a high value for its melting temperature, i.e., from 330 to 390° C. For example, the polysulfone resin is a polymer obtained by subjecting dichlorodiphenyl sulfone and bisphenol A, dihydroxydiphenyl sulfone, or 4,4-biphenol to polycondensation. Typical examples thereof include UDEL, RADEL, and VERADEL (Solvay Advanced Polymers), and ULTRASON (BASF). In addition, for example, ULTRASON S2010 has a glass transition temperature of 187° C. and a preferred melting temperature therefor is from 330 to 390° C.

One kind of the resin raw materials may be used alone, or two or more kinds thereof may be mixed and used.

The organic/inorganic composite of the present invention contains as a main component at least one kind selected from the polyarylketone resin and the polysulfone resin, and may further contain any other thermoplastic resin material as required. In this regard, however, preferred is a thermoplastic resin having such relatively high heat resistance that the resin raw material described above does not undergo pyrolysis at least during a kneading time at a temperature at which the resin raw material melts, that is, exhibits fluidity. Such resin is exemplified below.

A polyetherimide resin (PEI) is an amorphous thermoplastic resin having in a structural unit thereof an imide bond and an ether bond, and typical examples thereof include ULTEM (GE Plastics) and SUPERIO UT (Mitsubishi Plastics, Inc.).

A polyamideimide resin (PAI) is a thermoplastic resin having in a structural unit thereof an amide bond and an imide bond, and typical examples thereof include TORLON (Solvey Advanced Polymers) and TI Polymer (Toray Industries, Inc.).

A polyarylate resin, which is an aromatic polyester-based resin, is an amorphous thermoplastic resin produced by subjecting a dihydric phenol and a dibasic acid component to polycondensation. A typical example thereof is U-Polymer (UNITIKA LTD.).

A liquid crystal resin (LCP), which is an aromatic polyester-based resin, is different from the polyarylate resin in terms of having crystallinity. In general, polycondensates of p-hydroxybenzoic acid serving as a basic structure and the following compounds are known: ethylene terephthalate, phenol or biphenol and phthalic acid, or 2,6-hydroxynaphthoic acid. Typical examples thereof include VECTRA (Polyplastics Co., Ltd.) and SUMIKASUPER LCP (Sumitomo Chemical Company).

A polyphenylenesulfide resin (PPS) is a crystalline thermoplastic resin having a molecular structure in which a benzene ring and a sulfur atom are alternately bonded to each other. Typical examples thereof include DIC PPS (DIC) and TORELINA (Toray Industries, Inc.).

In addition, there are given polytetrafluoroethylene (PTFE), polychlorotrifluoroethylene (PCTFE), polyvinylidene fluoride (PVDF), polyamide (PA), polycarbonate (PC), polyethylene terephthalate (PET), polyphenylene ether (PPE), and polybutylene terephthalate (PBT).

One kind of those other thermoplastic resin materials may be used alone, or two or more kinds thereof may be as a mixture.

(B) Inorganic Particle Mixture (B) The inorganic particle mixture constituting the organic/inorganic composite according to this embodiment contains inorganic particles (B1) each having a particle diameter of from 200 to 700 nm at a content of 25 vol % or more, and inorganic particles (B2) each having a particle diameter of from 40 to 100 nm at a content of 10 vol % or more.

By blending the inorganic particles (B1) and the inorganic particles (B2) as described above, a high filling rate and dispersibility of the inorganic particles to be blended in the resin having a high melt viscosity can be secured. This is probably because: particles of a particle group having a relatively small particle diameter fill gaps between particles of a particle group having a relatively large particle diameter, thereby realizing close packing of the particles; and when a large number of fine inorganic particles are highly dispersed in a resin matrix, there is provided such an effect that in the application of a stress to the organic/inorganic composite body, the stress is dispersed in all directions. As a result, there is obtained an organic/inorganic composite having high mechanical strength, in which an abrupt increase in the viscosity of a molten resin due to the addition of inorganic particles is not caused, and hence the problem of a burnt resin due to the abrupt increase is suppressed, and which is excellent in mechanical strength. Regarding a preferred blending ratio between the inorganic particles (B1) and the inorganic particles (B2), the volume ratio of B1 with respect to the total volume of B1 and B2 is preferably from 0.6 to 0.8.

Regarding the particle size distribution of each of inorganic particles serving as raw materials for the components B1 and B2, the inorganic particles each more preferably have a sharp particle size distribution in which the coefficient of variation of the particle diameter is 0.3 or less from the viewpoint of close packing. In addition, the shape of each of the inorganic particles B1 and B2 is more preferably a substantially spherical shape. Herein, the substantially spherical shape means that, when a photograph of a filler is taken with a scanning electron microscope (hereinafter abbreviated as SEM), a particle observed within its unit field of view is rounded, and an average degree of symmetry, which is obtained by dividing a particle diameter in a direction perpendicular to that of its maximum diameter by the maximum diameter, is 0.6 or more. When inorganic particles each having a substantially spherical shape are used, highly close packing can be easily achieved. A manufacturing method for such inorganic particles each having a low coefficient of variation and a high average degree of symmetry is not particularly limited, but such inorganic particles may be suitably manufactured by, for example, a method described in JP 58-110414 A, JP 58-156524 A, or the like.

Further, inorganic particles (B3) each having a particle diameter of from 1 to 10 µm may be used as required. In this case, the inorganic particles (B3) each having a particle diameter of from 1 to 10 µm are preferably blended at from 10 to 55 vol % in the total amount of the inorganic mixed particles. This is because the specific surface area of the inorganic particles per unit volume lowers, and the inorganic mixed particles can be more uniformly dispersed in the molten resin. The further addition of the inorganic particles within such particle diameter range is expected to, while exhibiting close packing and stress dispersion effects, exhibit such an effect that even if a crack occurs, its extension is blocked by relatively large particles, thereby further improving mechanical strength.

When the blending ratio of the particles of 10 µm or more is high, mechanical strength may lower to the contrary from the viewpoints of reductions in particle close packing and stress dispersion effects.

The vol % of each particle diameter range in (B) the inorganic particle mixture may be measured using a particle size distribution analyzer. Specifically, (B) the inorganic particle mixture is added in ethanol serving as a dispersion medium, aggregated particles are sufficiently dispersed by ultrasonic irradiation, and then measurement is performed using a laser diffraction particle size distribution analyzer at least capable of measuring a particle diameter of 40 nm or more.

In this embodiment, the inorganic particle mixture is preferably contained at from 60 to 300 parts by mass with respect to 100 parts by mass of the resin raw material. The amount of the inorganic particle mixture is particularly preferably from 70 to 200 parts by mass, most preferably from 100 to 180 parts by mass with respect to 100 parts by mass of the resin raw material. In addition, when the amount of the inorganic particle mixture is 60 parts by mass or more, sufficient mechanical strength as an organic/inorganic composite is obtained. When the amount of the inorganic particle mixture is 300 parts by mass or less, the viscosity does not become excessively high at the time of mixing, and hence the filling rate and dispersibility of the mixed inorganic particles improve, and the problem of a burnt resin caused by an increase in viscosity can be avoided.

A material (component) for the inorganic particles is not particularly limited. Specifically, for example, the following materials may be used: silica glass, borosilicate glass, soda glass, aluminosilicate glass, fluoroaluminosilicate glass, and glass containing a heavy metal (such as barium, strontium, or zirconium); crystallized glass obtained by depositing a crystal in any such glass, and a glass ceramics such as crystallized glass obtained by depositing a crystal such as diopside or leucite; a composite inorganic oxide such as silica-zirconia, silica-titania, or silica-alumina; an oxide obtained by adding an oxide of a Group I metal to the composite inorganic oxide; and an inorganic oxide of a metal such as silica, alumina, titania, or zirconia. In the case of applying the organic/inorganic composite to be obtained to a dental material, because of low harmfulness to a living body and the like, silica-based particles formed of silica or a composite oxide of the silica with another metal oxide, and titanium dioxide-based particles formed of titania or a composite oxide of the titania with another metal oxide are suitable.

In addition, the surface of the component (B), i.e., the inorganic particle mixture is preferably hydrophobized for the purpose of improving its dispersibility in the component (A), i.e., the thermoplastic resin containing as a main component at least one kind selected from the resin raw materials. Such hydrophobization surface treatment is not particularly limited, and a known method may be adopted without any limitation. A typical surface treatment method is, for example, a method involving using a silane coupling agent or a titanate-based coupling agent as a hydrophobizing agent.

In particular, it is more preferred to use inorganic particles surface-treated with a surface treatment agent containing a (meth)acrylic group. It should be noted that the reason why the surface of the inorganic particle mixture surface-treated with a surface treatment agent containing a (meth)acrylic group has improved binding property with the resin is presumably because the (meth)acrylic group forms a cross-linked structure on a particle surface through a polymerization reaction to improve entanglement with the resin.

In this embodiment, the inorganic particles (B) are suitably surface-treated with a silane coupling agent represented by the following general formula (1).

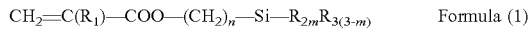

$$CH_2=C(R_1)-COO-(CH_2)_n-Si-R_{2m}R_{3(3-m)} \quad \text{Formula (1)}$$

(In the formula (1), $R_1$ represents a hydrogen atom or a methyl group, $R_2$ represents an alkoxy group having 1 to 6 carbon atoms, an isocyanate group, or a chlorine atom, $R_3$ represents a hydrocarbon group having 1 to 6 carbon atoms, m represents 1, 2, or 3, and n represents an integer of from 3 to 20.)

When the mixed inorganic particles are surface-treated with such silane coupling agent, an affinity between the mixed inorganic particles and the resin remarkably improves, which allows filling of the inorganic particles at a high rate, and thus the coefficient of thermal expansion of the organic/inorganic composite reduces, and its abrasion resistance improves, which is extremely advantageous in terms of, for example, an improvement in the durability of a blend material.

Examples of such silane coupling agent represented by the general formula (1) may include γ-methacryloyloxypropyltrimethoxysilane, hexamethyldisilazane, 10-methacryloyloxydecyltrimethoxysilane, 10-methacryloyloxydecylmethyldimethoxysilane, 10-methacryloyloxydecyltrichlorosilane, and 8-methacryloyloxyoctyltrimethoxysilane. One kind of those silane coupling agents may be used alone, or two or more kinds thereof may be mixed and used. In addition, in surface treatment using the silane coupling agent represented by the general formula (1), the amount of the silane coupling agent is not particularly limited. However, the amount suitably falls within the range of from 1 to 10 parts by mass with respect to 100 parts by mass of inorganic particles to be subjected to the surface treatment from the viewpoints of operability and physical properties of inorganic particles.

In the organic/inorganic composite body according to this embodiment, the inorganic fine particles are preferably highly dispersed individually. Herein, the highly dispersed state of the inorganic particles refers to a state in which individual primary particles in the inorganic fine particle mixture are dispersed in the resin without being aggregated, and further, the distributions of the particles B1 and B2 are not uneven. Whether or not such state is achieved may be confirmed by transmission electron microscope (TEM) observation.

In order to obtain such high dispersibility, it is preferred to adopt, in the manufacture of the inorganic fine particle mixture, a method involving performing dispersion to a primary particle level using a powerful disperser such as a bead mill, and then drying the resultant under a mild condition of less than 100° C. In addition, a method involving performing dispersion by applying a high shear force at the time of kneading with the resin may also be adopted.

In this embodiment, further, it is preferred that the organic/inorganic composite have a bending strength of 200 MPa or more, more preferably 210 MPa or more, a modulus of elasticity of 6 GPa or more, more preferably 10 GPa or more, and a fracture energy of 5 N/mm or more, more preferably 7 N/mm. The organic/inorganic composite having all of such mechanical strengths shows properties of having strong resistance to a load, being hardly deflected, and being hardly fractured, and has high durability even in a severe environment. Accordingly, the organic/inorganic composite can be effectively used particularly as a dental material or a bone substitute material.

In the case of using the organic/inorganic composite body according to this embodiment as a dental material, the organic/inorganic composite body can be suitably used for, for example, a denture, an artificial tooth, a denture base, a dental implant (fixture, abutment, or superstructure), a crown restoration material, or a core build-up material. The organic/inorganic composite body according to this embodiment has similar dynamic characteristics to those of a natural tooth or alveolar bone as compared to a metal or ceramic material, and to other resin materials, and hence is extremely useful not only from the viewpoint of its high mechanical characteristics but also from the viewpoint of biocompatibility such as being free of harmfulness to a living body as observed in a metal material (such as stress concentration due to a difference in modulus of elasticity, stress shielding, or allergy). In a case for which there has been no choice but to select a metal because of a problem in mechanical strength, the organic/inorganic composite body can be used as a substitute material therefor.

In addition, in the case of using the organic/inorganic composite body according to this embodiment as a bone substitute material (artificial bone or implant), the organic/inorganic composite body can be usefully used as an artificial bone, an artificial joint, or any of other various non-removable implant materials. The organic/inorganic composite body according to this embodiment is particularly excellent because the organic/inorganic composite body has more flexibility than a metal or ceramic material, and hence has more similar dynamic characteristics to those of bone itself, hardly involving problems due to differences in physical properties such as stress shielding.

Next, an apparatus for manufacturing the organic/inorganic composite according to this embodiment is described. A manufacturing method for the organic/inorganic composite is not particularly limited, but a kneading apparatus that includes a raw material supply unit for feeding (A) the resin raw material and (B) the inorganic particle mixture, a melt-kneading unit for mixing these components, and a molding unit for discharging an organic/inorganic composite body to mold it into a certain shape, in an integral or separate manner, is suitably used.

As the raw material supply unit, a known supply apparatus may be used. Manually mixed raw materials may be directly fed to the melt-kneading unit. In order to prevent uneven distribution of (A) the resin raw material and (B) the inorganic particle mixture, it is preferred to use a small-amount automatic weighing type auto-feeder or the like.

In the melt-kneading unit, the resin is heated and melted, and is conformed to the inorganic particles, and the molten resin and the inorganic particles are further mixed by applying a shear force to generate an organic/inorganic composite melt. The heating and melting and the shear mixing may be simultaneously performed while transfer to the molding unit is performed in a screw shape. Alternatively, the following design may be adopted: after the resin has been sufficiently melted in advance, shear is sufficiently applied in the kneading unit. When a plasticizing unit and the kneading unit are separately provided as in the latter case, high dispersibility of the inorganic particle mixture is more easily obtained. In addition, the kneading may be performed in a continuous mode or a batch mode, but the application of repeated shear in a batch mode is likely to result in more satisfactory dispersion.

In the molding unit, the organic/inorganic composite body melt is recovered, and is cooled and molded into a desired shape. Any method such as injection molding, press molding, extrusion molding, or transfer molding may be adopted. The shape of the organic/inorganic composite body to be obtained may adopt any of various forms such as a massive shape, a film plate, a plate shape, a pellet shape, a string shape, and a powder shape, depending on the structure of the molding unit. An organic/inorganic composite body having a required shape may be continuously obtained by producing a mold of a desired shape and connecting the mold to the molding unit. Alternatively, an organic/inorganic composite body in a state of a massive shape, a pellet shape, a string shape, or a powder shape may be recovered once, and may be remolded into an arbitrary shape as required.

Figure 2:
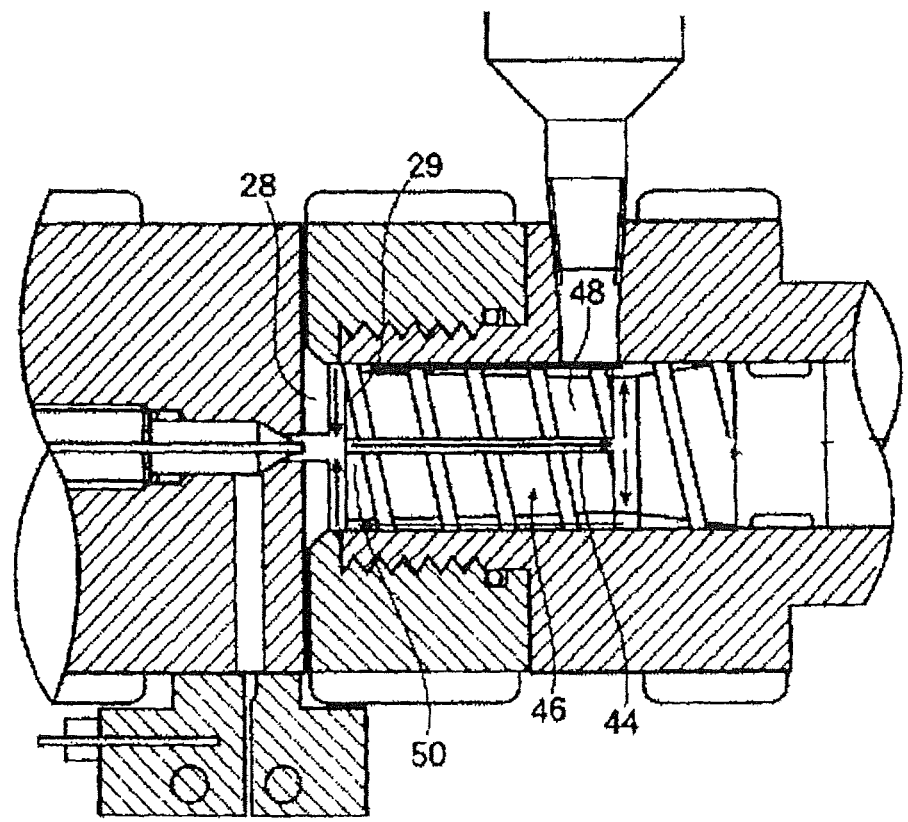
FIG. 2 is a view illustrating an internal-return screw of a melt-kneading unit of the apparatus illustrated in FIG. 1.
Figure 3:
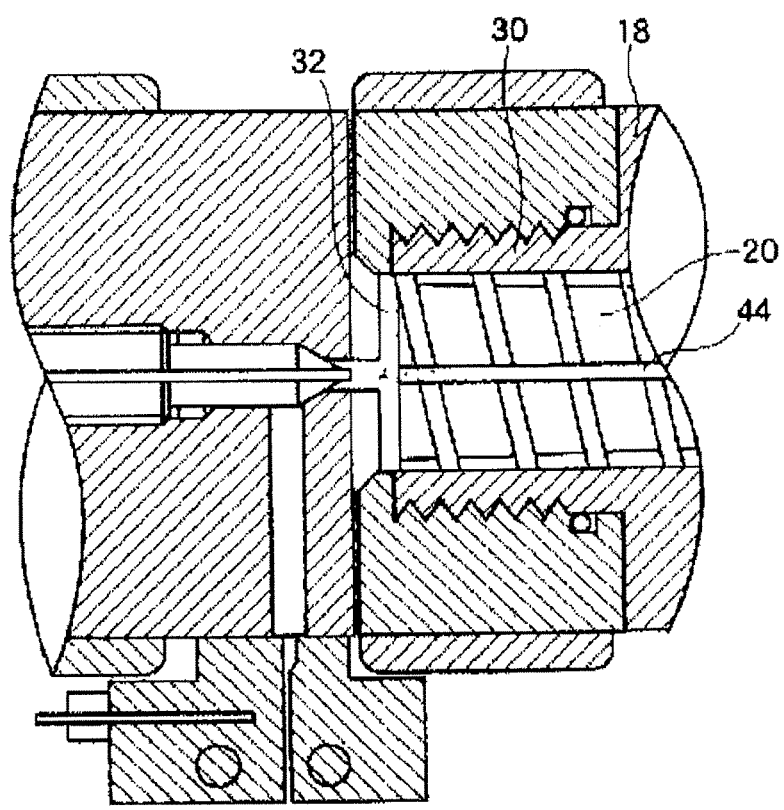
FIG. 3 is a view illustrating a gap in the front end of the internal-return screw of the melt-kneading unit of the apparatus illustrated in FIG. 1.

FIGS. 1 to 3 illustrate an example of a melt-kneading apparatus. FIG. 1 is an overall view of an apparatus for manufacturing an organic/inorganic composite having mixed inorganic particles uniformly dispersed in a thermoplastic resin containing as a main component at least one kind selected from a polyarylketone resin and a polysulfone resin (melt-kneaded product and molded product). FIG. 2 is a view illustrating an internal-return screw of a melt-kneading unit of the apparatus illustrated in FIG. 1. FIG. 3 is a view illustrating a gap in the front end of the internal-return screw of the melt-kneading unit of the apparatus illustrated in FIG. 1.

As illustrated in FIGS. 1 to 3, a melt-kneaded product-manufacturing apparatus 10 includes a raw material supply unit 16 for mixed inorganic particles and a resin raw material, a melt-kneading unit 12, and a molding unit 14. The resin raw material and inorganic particles in a molten state are fed from the raw material supply unit 16.

The melt-kneading unit 12 includes an internal-return screw 20 in a cylinder 18. The internal-return screw 20 is provided in the cylinder 18 through a shaft 24. The shaft 24 communicates with the internal-return screw 20 through a bearing 22. In addition, along the outside of the cylinder 18, there is provided a heater 26 for melting the resin raw material. At the end of the cylinder 18 opposite to the position of the shaft 24, there is provided a seal 28 for sealing the melt-kneading unit 12 and the molding unit 14 together. In addition, in the cylinder 18, control means 30 for controlling a gap 32 is provided between a tip end surface 29 of the internal-return screw 20 and the surface of the seal 28. The gap 32 may be controlled within the range of from 0.5 mm to 5 mm.

The molding apparatus 14 includes an extrusion unit heater 35 and a T-die 34. The T-die 34 includes a T-die front end heating heater 36 and a T-die back end heating heater 38. An extruded film passes through a discharge port 40 formed between the T-die front end heating heater 36 and the T-die back end heating heater 38. A thermocouple 42 for temperature measurement is inserted in the molding unit and the T-die front end heating heater. The result of the measurement is transferred to a control apparatus (not shown), and the temperatures of the melt-kneading unit 12 and the T-die are adjusted.

The screw 20 includes in itself an inner slot 44 having an inner diameter of from 1 mm to 5 mm, preferably from 2 mm to 3 mm. The internal-return screw 20 has an L/D ratio (L: length, D: diameter) of 1.78. The rotation speed of the screw is adjusted within the range of from 300 rpm to 3,000 rpm. The shear rate may be adjusted within the range of from 450 to 4,500 $sec^{-1}$. The temperature in the cylinder varies depending on the resin raw material to be melted.

The screw has a structure sufficient to melt the resin raw material in the cylinder. FIG. 2 illustrates a structure 46 of the internal-return screw. In the structure 46 of the internal-return screw, the resin raw material supplied from a screw back portion 48 is transferred to a screw front portion 50 by the screw. The molten resin is confined in the gap 32 formed between the front surface 29 and a seal surface 31. The resin passes, via the slot 44 in a lateral direction provided in the central portion of the screw, through a slot in a different direction, and is directed, via the screw back portion 48, back to the front direction 50 of the screw.

A period of time required for shear melting can be changed by a period of time required for circulation in the structure 46 of the internal-return screw. The extent to which the resin is sheared can be controlled by changing the gap formed between the screw back end and the seal surface leading to the diameter inside the screw. The extent to which the resin is sheared can be increased by narrowing the gap or narrowing the diameter of the slot. The inner diameters of the gap and the slot of the screw need to be optimized in view of the viscosity of the resin. A period of time required for melt-kneading of the resin contained in the cylinder is from 1 minute to 8 minutes. The melt-kneading of the resin raw material and the inorganic particle mixture through the use of such melt-kneaded product-manufacturing apparatus is preferred because the organic/inorganic composite to be generally obtained is the one excellent in mechanical strengths having a bending strength of 200 MPa or more, a modulus of elasticity of 6 GPa or more, and a fracture energy of 5 N/mm or more described above.

Hereinafter, a manufacturing method for the organic/inorganic composite according to this embodiment of the present invention is described. That is, raw materials including (A) 100 parts by mass of the thermoplastic resin containing as a main component at least one kind selected from the polyarylketone resin and the polysulfone resin, and (B)

60 to 300 parts by mass of the inorganic particle mixture containing particles each having a particle diameter of from 200 to 700 nm at a content of 25 mass % or more, and particles each having a particle diameter of from 40 to 100 nm at a content of 10 mass % or more are, as required, premixed or fed from the raw material feeding unit 16 using a feeder with a weighing function, and are supplied to the melt-kneading unit 12 including a heating unit in the cylinder including the screw 20. The melt heating temperature is set to a condition of from 200 to 500° C. The raw materials are transferred to a forward direction by the action of the internal-return screw 20.

A melt-kneaded resin obtained by treatment under the conditions of a rotation number of the screw of from 300 rpm to 3,000 rpm, preferably from 500 rpm to 1,500 rpm, and a shear rate of from 450 to 4,500 $sec^{-1}$, preferably from 750 to 2,250 $sec^{-1}$ is transferred from the rear end of the screw to the forward end. The melt-kneaded resin is confined in the gap 32 of the forward end of the screw, and then transferred from the gap 32 through the slot 44 provided at the central portion of the screw to the rear end of the screw. The gap 32 can be controlled within the range of from 0.5 mm to 5 mm.

The mixed particles in a state of being uniformly dispersed in the molten resin raw material pass through the slot 44 in a lateral direction provided at the central portion of the screw, are confined in the screw rear end, and are recirculated and transferred via the screw back portion 48 back to the screw front portion 50 with the screw. The repetitive circulation is performed for from 10 seconds to 10 minutes, preferably from 30 seconds to 5 minutes, more preferably from 1 minute to 2 minutes to achieve a more uniformly dispersed state of the mixed particles in the molten resin raw material.

In order to apply an effective shear force and enhance the dispersibility of the inorganic particles, it is preferred that the rotation number of the screw be 300 rpm or more and the shear rate be 450 $sec^{-1}$ or more. On the other hand, in order to avoid a burnt resin or pyrolysis due to an increase in resin temperature, it is preferred that the rotation number of the screw be less than 3,000 rpm and the shear rate be less than 4,500 $sec^{-1}$. Regarding the shape of the screw, one having a generally used shape except for the presence of the slot for feeding back the sample is used.

The circulation operation at the interval as described above is repeated to achieve a more uniformly dispersed state of the mixed particles in the molten resin material, and the dispersion is taken out to the molding apparatus 14 via the gap 28. In this case, the dispersion is taken out to the molding apparatus 14 by opening a valve (not shown). The thermocouple 42 for temperature measurement is inserted in the molding unit and the T-die front end heating heater. The result of the measurement is transferred to a control apparatus (not shown), and the temperatures of the melt-kneading unit 12 and the T-die are adjusted.

As an apparatus to be used in the melt-kneading step for manufacturing the organic/inorganic composite according to this embodiment, any known melt-kneading apparatus may be used without any particular limitation. For example, an apparatus that is not limited to the application of a shear flow field but is capable of applying an elongation field is suitable. For example, in FIG. 2, a shear flow field is applied between the screw and the cylinder, and an elongation field is applied upon passage through the screw return slit 44. An apparatus capable of applying such fields is suitable. A single-screw melt-kneading apparatus, a twin-screw melt-kneading apparatus, or the like may be used. In addition, after the melt-kneading step, various post-processes may be carried out as required. For example, the melt-kneaded product in a high-temperature state immediately after the melt-kneading step may be directly subjected to injection molding, extrusion molding, or the like to be molded into a given shape. In addition, the melt-kneaded product in a high-temperature state immediately after the melt-kneading step may be first molded into a member for secondary processing having a pellet shape, a powder shape, a block shape, or the like, and then the member for secondary processing may be further subjected to any of various types of processing such as injection molding, extrusion molding, laser forming, cutting processing, machining processing, and polishing processing.

When the organic/inorganic composite material according to this embodiment is molded into a finished molded body by any of various molding methods such as injection molding, extrusion molding, and compression molding, the productivity of the molded body can be enhanced by performing rapid cooling in the mold. In such case, the rapid cooling may cause a residual stress inside the molded body, and the crystal structure of a crystalline resin may not be formed in an ideal manner. In order to solve those problems, in the organic/inorganic composite material according to this embodiment, the obtained molded body may be subjected to heat treatment as required. When the heat treatment is performed, a residual stress inside the molded body can be released. In addition, when a polyarylketone resin is used, the recrystallization of the resin vitrified by the rapid cooling can be promoted, and as a result, the mechanical strength of the molded body can be enhanced.

A method for the heat treatment is not particularly limited, but the temperature is preferably selected from a temperature region of the glass transition temperature or more where the melt viscosity is not exceeded, and is preferably selected from the range of from 150 to 300° C. The heat treatment time is preferably selected from the range of from 30 minutes to 6 hours. A cooling step after the heat treatment preferably involves leaving the molded body in a heating apparatus such as an oven in which the heat treatment has been performed under a state in which its heat source is turned off to return the temperature to room temperature over a period of time of 1 hour or more.

In addition, for the same reason, when the organic/inorganic composite material according to this embodiment is molded into a finished molded body by a molding method such as injection molding, extrusion molding, or compression molding, it is also possible to obtain a finished molded article having high strength from the melt by the same slow cooling method as described above without performing the heat treatment step.

EXAMPLES

Hereinafter, the present invention is specifically described by way of Examples. However, the present invention is not limited to Examples shown below.

Inorganic particle mixture manufacturing methods, an organic/inorganic composite preparation method, and an organic/inorganic composite evaluation method are described below.

(1) Inorganic Particle Mixture Manufacturing Method

Manufacturing Example 1

Manufacturing Method for (B) Inorganic Particle Mixture F1

80 g of tetraethyl silicate (manufactured by NIPPON COLCOAT CO., LTD., product name: Ethyl Silicate 28) were mixed with 400 g of isobutyl alcohol (manufactured by TonenGeneral Sekiyu K.K), 5 g of a 0.05% sulfuric acid aqueous solution were added thereto, and the mixture was subjected to hydrolysis at 40° C. for about 1 hour while being stirred. After that, the stirred solution was mixed with a solution obtained by dissolving 35 g of tetrabutyl zirconate (manufactured by Nippon Soda Co., Ltd.) and a solution of sodium methylate in methanol (concentration: 28 wt %) in 200 g of isobutyl alcohol to prepare a mixed solution of tetraethyl silicate and tetrabutyl zirconate. Next, 1,000 g isobutyl alcohol and 250 g of 25% ammonia water were introduced into a glass vessel having an internal volume of 3 L with a stirring apparatus. 4 g of tetraethyl silicate were added to the stirred ammoniacal alcohol solution in the glass vessel, and the mixture was stirred for 30 minutes. After that, the mixed solution of tetraethyl silicate and tetrabutyl zirconate was added dropwise over about 6 hours. It should be noted that the temperature of the reaction vessel was kept at 40° C. during the reaction. After the completion of the reaction, the solvent was evaporated from the liquid, which had become cloudy, in the reaction vessel, and the residue was dried and was fired at 950° C. for 1 hour to provide silica-zirconia particles (A-1). The silica-zirconia particles each had an average primary particle diameter of 420 nm, had a spherical shape, and had a coefficient of variation of the particle diameter of 0.13.

Silica-zirconia particles (A-2) were obtained in the same manner as in the method described above except that, after 1,000 g of methanol and 200 g of 25% ammonia water had been introduced into a glass vessel having an internal volume of 3 L with a stirring apparatus, tetraethyl silicate was not added to the ammoniacal alcohol solution, and the mixed solution of tetraethyl silicate and tetrabutyl zirconate was added dropwise over about 3 hours. The silica-zirconia particles each had an average primary particle diameter of 70 nm, and had a spherical shape.

700 g of the spherical silica-zirconia particles (A-1) each having an average primary particle diameter of 420 nm and 300 g of the spherical silica-zirconia particles (A-2) each having an average primary particle diameter of 70 nm were introduced into 4 L of a pure water solvent, and the particles were dispersed using an ultra-high pressure impact type emulsifying disperser Nanomizer at a treatment pressure of 60 MPa. Surface treatment was performed using γ-methacryloxypropyltrimethoxysilane, and then the solvent was evaporated and the residue was dried to provide an inorganic composition. The pore size distribution of the inorganic composition was measured and the results were as follows: the volume of strongly aggregated pores each having a pore size of 0.08 µm or more was 0.01 cc/g, and the volume of strongly aggregated pores each having a pore size of from 0.008 to 0.064 µm was 0.03 cc/g. The inorganic composition was defined as an inorganic particle mixture F1.

Manufacturing Example 2

Manufacturing Method for (B) Inorganic Particle Mixture F2

800 g of the spherical silica-zirconia particles (A-1) each having an average primary particle diameter of 420 nm and 200 g of the spherical silica-zirconia particles (A-2) each having an average primary particle diameter of 70 nm were introduced into 4 L of a pure water solvent, and the particles were dispersed using an ultra-high pressure impact type emulsifying disperser Nanomizer at a treatment pressure of 60 MPa. Surface treatment was performed using γ-methacryloxypropyltrimethoxysilane, and then the solvent was evaporated and the residue was dried to provide an inorganic composition. The pore size distribution of the inorganic composition was measured and the results were as follows: the volume of strongly aggregated pores each having a pore size of 0.08 µm or more was 0.01 cc/g, and the volume of strongly aggregated pores each having a pore size of from 0.008 to 0.064 µm was 0.03 cc/g. The inorganic composition was defined as an inorganic particle mixture F2.

Manufacturing Example 3

Manufacturing Method for (B) Inorganic Particles F3

500 g of the spherical silica-zirconia particles (A-1) each having an average primary particle diameter of 420 nm and 500 g of the spherical silica-zirconia particles (A-2) each having an average primary particle diameter of 70 nm were introduced into 4 L of a pure water solvent, and the particles were dispersed using an ultra-high pressure impact type emulsifying disperser Nanomizer at a treatment pressure of 60 MPa. Surface treatment was performed using γ-methacryloxypropyltrimethoxysilane, and then the solvent was evaporated and the residue was dried to provide an inorganic composition. The pore size distribution of the inorganic composition was measured and the results were as follows: the volume of strongly aggregated pores each having a pore size of 0.08 µm or more was 0.01 cc/g, and the volume of strongly aggregated pores each having a pore size of from 0.008 to 0.064 µm was 0.03 cc/g. The inorganic composition was defined as an inorganic particle mixture F3.

Manufacturing Example 4

Manufacturing Method for (B) Inorganic Particles F4

At room temperature, 60 ml of 0.005% dilute sulfuric acid were added to a solution obtained by dissolving 1,600 g of tetraethyl silicate (manufactured by NIPPON COLCOAT CO., LTD.) in 2.0 l of isobutanol, and the mixture was stirred for 3 hours to be subjected to partial hydrolysis. After that, 670 g of tetrabutyl zirconate and 77 g of sodium methylate were added. Stirring was continued for 1 hour, and then 0.3 L of water was added under stirring to perform further hydrolysis, thereby providing a gel. Next, the gel was taken out, and dried by heating at 100° C. to remove the solvent. Thus, a dry gel was obtained. The dry gel was pulverized with a ball mill. The pulverized product, which had been coarsely pulverized with the ball mill to 1,000 µm or less, was pulverized with a jet mill (manufactured by SEISHIN ENTERPRISE Co., Ltd., model: FS-4) under the condition of a nozzle pressure of 6 kg/cm². The obtained pulverized product was fired at 940° C. for 1 hour to provide white powder. The white powder was classified by elutriation to provide inorganic particles each having a desired average primary particle diameter. Further, the obtained respective particles were subjected to surface treatment using γ-methacryloyloxypropyltrimethoxysilane. The inorganic particles (A-3) each had an average primary particle diameter of 2.5

μm, and the ratio of particles of 10 μm or more was 0 vol %. The inorganic particles and the inorganic particle mixture F1 obtained in Manufacturing Example 1 were mixed at a mass ratio of 50:50, and the mixture was defined as an inorganic particle mixture F4.

Manufacturing Example 5

Manufacturing Method for (B) Inorganic Particles F5

The inorganic particles A-3 and the inorganic particle mixture F1 obtained in Manufacturing Example 1 were mixed at a mass ratio of 30:70, and the mixture was defined as an inorganic particle mixture F5.

Manufacturing Example 6

Manufacturing Method for (B) Inorganic Particles F6

The inorganic particles A-3 and the inorganic particle mixture F1 obtained in Manufacturing Example 1 were mixed at a mass ratio of 40:60, and the mixture was defined as an inorganic particle mixture F6.

Manufacturing Example 7

Manufacturing Method for (B) Inorganic Particles F7

The inorganic particles (A-3) and the inorganic particle mixture F3 obtained in Manufacturing Example 3 were mixed at a mass ratio of 40:60, and the mixture was defined as an inorganic particle mixture F7.

Manufacturing Example 8

Manufacturing Method for (B) Inorganic Particles F8

1 kg of the spherical silica-zirconia particles (A-1) each having an average primary particle diameter of 420 nm was introduced into 4 L of a pure water solvent, and subjected to surface treatment using γ-methacryloxypropyltrimethoxysilane. After that, the solvent was removed, and the residue was further dried to provide an inorganic composition, which was defined as inorganic particles F8.

Manufacturing Example 9

Manufacturing Method for (B) Inorganic Particles F9

Amorphous spherical silica having an average particle diameter of 3 microns was manufactured by a gas phase reaction using silicon tetrachloride as a raw material. The silica was subjected to surface treatment using γ-methacryloxypropyltrimethoxysilane, and then the solvent was removed and the residue was further dried to provide an inorganic composition, which was defined as inorganic particles F9.

Manufacturing Example 10

Manufacturing Method for (B) Inorganic Particles F10

At room temperature, 60 ml of 0.005% dilute sulfuric acid were added to a solution obtained by dissolving 1,600 g of tetraethyl silicate (manufactured by NIPPON COLCOAT CO., LTD.) in 2.0 l of isobutanol, and the mixture was stirred for 3 hours to be subjected to partial hydrolysis. After that, 670 g of tetrabutyl zirconate and 77 g of sodium methylate were added. Stirring was continued for 1 hour, and then 0.3 L of water was added under stirring to perform further hydrolysis, thereby providing a gel. Next, the gel was taken out, and dried by heating at 100° C. to remove the solvent. Thus, a dry gel was obtained. The dry gel was pulverized with a ball mill. The pulverized product, which had been coarsely pulverized with the ball mill to 1,000 μm or less, was pulverized with a jet mill (manufactured by SEISHIN ENTERPRISE Co., Ltd., model: FS-4) under the condition of a nozzle pressure of 6 kg/cm$^2$. The obtained pulverized product was fired at 940° C. for 1 hour to provide white powder. The white powder was classified by elutriation to provide inorganic particles each having a desired average primary particle diameter. Further, the obtained respective particles were subjected to surface treatment using γ-methacryloyloxypropyltrimethoxysilane. The inorganic particles each had an average primary particle diameter of 1.1 μm, and the ratio of particles of 10 μm or more was 0 vol %. The inorganic particles were defined as an inorganic particle mixture F10.

(2) Preparation Method for Organic/Inorganic Composite (A) The thermoplastic resin and (B) the inorganic particle mixture were weighed and premixed in a plastic cup with a spatula, and the mixture was fed to a kneader NHSS2-28 (manufactured by NIIGATA MACHINE TECHNO CO., LTD.) through a raw material feeding unit. The resin was plasticized at a screw temperature of from 350 to 400° C., followed by mixing in a kneading unit at a set rotation number for a set period of time, and extruded from a discharge unit to provide an organic/inorganic composite in which the thermoplastic resin and the inorganic particle mixture were mixed. The organic/inorganic composite was cut into a pellet shape of from about 3 to 5 mm, subjected to compression molding using a hot press machine set to 350° C., and slowly cooled under room temperature to produce a plate-shaped molded body measuring 50×25×2 mm.

(3) Evaluation Method for Organic/Inorganic Composite Evaluation Method for Bending Strength, Modulus of Elasticity, and Fracture Energy An injection-molded body having a thickness of 2 mm was cut at intervals of 2 mm using a rotary diamond cutter while water was poured to prepare five rod-shaped test pieces each having a length of 25 mm, a width of 2 mm, and a thickness of 2 mm for each sample. Burrs on the samples were removed using #800 waterproof abrasive paper, the width and thickness of the central portion of each test piece were measured with a micrometer, and a three-point bending test was performed with a universal testing machine AG-50kI (SHIMADZU CORPORATION) at room temperature in the air under the conditions of a support distance of 20 mm and a crosshead speed of 1 mm/min to prepare a stress-strain curve.

A bending strength was determined from the following equation.

$$\sigma_B = 3PS/2WB^2$$

In the equation, $\sigma_B$ represents a bending strength (Pa), P represents a load (N) at the time of the breakage of the test piece, S represents a support distance (m), W represents a width (m) of the test piece, and B represents a thickness (m) of the test piece.

In addition, a bending modulus of elasticity was determined from the following equation. A load of from 5 N to 10 N was used for the calculation.

$$E_B = (S^3 \cdot F)/(4WB^3 \cdot Y)$$

In the equation, $E_B$ represents a bending modulus of elasticity (Pa), and Y represents a bending deflection (m).

In addition, energy [N·m] consumed for fracture was determined from the integrated value of the stress-strain curve up to a fracture point, and was divided by the cross-sectional area of the sample to determine fracture energy [N/mm].

Example 1

100 parts by mass of PEEK 90G (manufactured by Victrex plc, melt viscosity at 400° C.: 100 Pa·S) as (A) the thermoplastic resin and 60 parts by mass of F1 as (B) the inorganic particle mixture were weighed and premixed in a plastic cup using a spatula. The mixture was fed to a kneader NHSS2-28 (manufactured by NIIGATA MACHINE TECHNO CO., LTD.) serving as the melt-kneading apparatus illustrated in FIGS. 1 to 3 through the raw material feeding unit. The resin was plasticized at a screw temperature of from 350 to 400° C., followed by mixing in the kneading unit under the condition of a rotation number of 1,000 rpm for 30 seconds, and extruded from the discharge unit to provide an organic/inorganic composite in which the thermoplastic resin and the inorganic particle mixture were mixed. The organic/inorganic composite was cut into a pellet shape of from about 3 to 5 mm, and subjected to compression molding using a pressing machine to produce a plate-shaped molded body measuring 50×25×2 mm. Table 1 shows the composition, and Table 2 shows the manufacture conditions and the evaluation result.

TABLE 1

|  | (A) Thermoplastic resin | (B) Inorganic particle mixture | (B1) 200 to 700 nm Volume ratio | (B2) 30 to 100 nm Volume ratio | (B3) 1 to 10 μm Volume ratio | B1/ (B1 + B2) | (A) Thermoplastic resin Parts by mass | (B) Inorganic particle mixture Parts by mass |
|---|---|---|---|---|---|---|---|---|
| Example 1 | P1 | F1 | 71 | 29 | 0 | 0.71 | 100 | 60 |
| Example 2 | P1 | F1 | 71 | 29 | 0 | 0.71 | 100 | 60 |
| Example 3 | P1 | F1 | 71 | 29 | 0 | 0.71 | 100 | 150 |
| Example 4 | P1 | F1 | 71 | 29 | 0 | 0.71 | 100 | 150 |
| Example 5 | P1 | F1 | 71 | 29 | 0 | 0.71 | 100 | 150 |
| Example 6 | P1 | F1 | 71 | 29 | 0 | 0.71 | 100 | 200 |
| Example 7 | P1 | F1 | 71 | 29 | 0 | 0.71 | 100 | 200 |
| Example 8 | P1 | F2 | 80 | 20 | 0 | 0.85 | 100 | 150 |
| Example 9 | P1 | F3 | 50 | 50 | 0 | 0.52 | 100 | 150 |
| Example 10 | P1 | F4 | 36 | 15 | 45 | 0.71 | 100 | 60 |
| Example 11 | P1 | F4 | 36 | 15 | 45 | 0.71 | 100 | 150 |
| Example 12 | P1 | F4 | 36 | 15 | 45 | 0.71 | 100 | 150 |
| Example 13 | P1 | F4 | 36 | 15 | 45 | 0.71 | 100 | 200 |
| Example 14 | P1 | F4 | 36 | 15 | 45 | 0.71 | 100 | 200 |
| Example 15 | P1 | F5 | 49 | 21 | 30 | 0.70 | 100 | 150 |
| Example 16 | P1 | F6 | 45 | 15 | 40 | 0.75 | 100 | 150 |
| Example 17 | P1 | F7 | 30 | 30 | 40 | 0.50 | 100 | 150 |
| Comparative Example 1 | P1 | F1 | 71 | 29 | 0 | 0.71 | 100 | 40 |
| Comparative Example 2 | P2 | — | 0 | 0 | 0 | — | 100 | 30 |
| Comparative Example 3 | P1 | F1 | 71 | 29 | 0 | 0.71 | 100 | 350 |
| Comparative Example 4 | P1 | F8 | 100 | 0 | 0 | 1.00 | 100 | 150 |
| Comparative Example 5 | P1 | F9 | 3 | 0 | 94 | 1.00 | 100 | 60 |
| Comparative Example 6 | P1 | F10 | 33 | 0 | 47 | 1.00 | 100 | 150 |

TABLE 2

|  | Rotation number (rpm) | Kneading temperature (° C.) | Treatment time (s) | Shear rate (s⁻¹) | Bending strength [MPa] | Modulus of elasticity [GPa] | Fracture energy [N/mm] |
|---|---|---|---|---|---|---|---|
| Example 1 | 1,000 | 350 to 400 | 30 | 1,500 | 182 | 6.1 | 11.2 |
| Example 2 | 2,000 | 350 to 400 | 30 | 3,000 | 198 | 6.3 | 15.3 |
| Example 3 | 500 | 350 to 400 | 30 | 750 | 181 | 7.9 | 8.2 |
| Example 4 | 1,000 | 350 to 400 | 30 | 1,500 | 193 | 8.1 | 9.1 |
| Example 5 | 800 | 350 to 400 | 120 | 1,200 | 205 | 8.3 | 9.4 |
| Example 6 | 300 | 350 to 400 | 120 | 450 | 182 | 9.3 | 6.7 |
| Example 7 | 600 | 350 to 400 | 120 | 900 | 209 | 11.0 | 9.2 |
| Example 8 | 1,000 | 350 to 400 | 30 | 1,500 | 185 | 8.4 | 6.7 |
| Example 9 | 1,000 | 350 to 400 | 30 | 1,500 | 182 | 8.6 | 6.8 |
| Example 10 | 800 | 350 to 400 | 120 | 1,200 | 208 | 6.4 | 20.9 |
| Example 11 | 300 | 350 to 400 | 120 | 450 | 187 | 9.4 | 7.0 |

TABLE 2-continued

|  | Rotation number (rpm) | Kneading temperature (° C.) | Treatment time (s) | Shear rate (s⁻¹) | Bending strength [MPa] | Modulus of elasticity [GPa] | Fracture energy [N/mm] |
|---|---|---|---|---|---|---|---|
| Example 12 | 800 | 350 to 400 | 120 | 1,200 | 208 | 10.6 | 9.5 |
| Example 13 | 300 | 350 to 400 | 120 | 450 | 193 | 10.8 | 6.4 |
| Example 14 | 600 | 350 to 400 | 120 | 900 | 218 | 11.6 | 8.8 |
| Example 15 | 800 | 350 to 400 | 120 | 1,200 | 209 | 9.8 | 7.8 |
| Example 16 | 800 | 350 to 400 | 120 | 1,200 | 211 | 10.7 | 8.0 |
| Example 17 | 800 | 350 to 400 | 120 | 1,200 | 193 | 10.4 | 6.4 |
| Comparative Example 1 | 1,000 | 350 to 400 | 30 | 1,500 | 183 | 5.3 | 11.9 |
| Comparative Example 2 | 1,000 | 350 to 400 | 30 | 1,500 | 165 | 7.5 | 4.9 |
| Comparative Example 3 | 1,000 | 350 to 400 | 30 | 1,500 | The amount of the inorganic particles was so large that kneading was not able to be performed | | |
| Comparative Example 4 | 1,000 | 350 to 400 | 30 | 1,500 | 147 | 10.9 | 2.6 |
| Comparative Example 5 | 800 | 350 to 400 | 120 | 1,200 | 176 | 6.2 | 8.9 |
| Comparative Example 6 | 1,000 | 350 to 400 | 30 | 1,500 | 171 | 10.3 | 4.7 |

Examples 2 to 17

Each plate-shaped molded body was produced in the same manner as in Example 1 except that the composition and manufacture conditions were set as shown in Tables 1 and 2. In addition, Table 2 also shows the evaluation results.

Comparative Examples

Comparative Example 1

A plate-shaped molded body was produced in the same manner as in Example 1 except that 100 parts by mass of PEEK 90G (manufactured by Victrex plc) as (A) the thermoplastic resin and 40 parts by mass of F1 as (B) the inorganic particle mixture were weighed. Table 2 shows the evaluation results.

Comparative Example 2

A plate-shaped molded body was produced in the same manner as in Example except that as (A) the thermoplastic resin, PEEK 90GL30 (manufactured by Victrex plc) containing 30 mass % of a glass fiber filler was used. Table 2 shows the evaluation results.

Comparative Examples 3 to 6

Each plate-shaped molded body was produced in the same manner as in Example 1 except that the composition and manufacture conditions were set as shown in Tables 1 and 2. In addition, Table 2 also shows the evaluation results.

The invention claimed is:

1. An organic/inorganic composite, comprising:
(A) 100 parts by mass of a thermoplastic resin containing as a main component at least one kind selected from a polyarylketone resin and a polysulfone resin; and
(B) 60 to 300 parts by mass of an inorganic particle mixture dispersed in the thermoplastic resin,
wherein the inorganic particle mixture contains inorganic particles (B1) each having a particle diameter of from 200 to 700 nm at a content of 25 vol % or more, and inorganic particles (B2) each having a particle diameter of from 40 to 100 nm at a content of 10 vol % or more, and
wherein a volume ratio of the inorganic particles (B1) with respect to a total volume of the inorganic particles (B1) and the inorganic particles (B2) is from 0.6 to 0.8.

2. The organic/inorganic composite according to claim 1, wherein (B) the inorganic particle mixture further contains inorganic particles each having a particle diameter of from 1 to 10 μm at a content of from 10 to 55 vol %.

3. The organic/inorganic composite according to claim 1, wherein the inorganic particles constituting (B) the inorganic particle mixture comprise silica-based inorganic particles.

4. The organic/inorganic composite according to claim 1, wherein the inorganic particles comprise titanium dioxide-based particles.

5. The organic/inorganic composite according to claim 1, wherein (A) the resin comprises polyetheretherketone.

6. The organic/inorganic composite according to claim 1, wherein the organic/inorganic composite has a bending strength of 200 MPa or more, a modulus of elasticity of 6 GPa or more, and a fracture energy of 5 N/mm or more.

7. A manufacturing method for an organic/inorganic composite, comprising melt-kneading raw materials including
(A) 100 parts by mass of a thermoplastic resin containing as a main component at least one kind selected from a polyarylketone resin and a polysulfone resin, and
(B) 60 to 300 parts by mass of an inorganic particle mixture containing inorganic particles (B1) each having a particle diameter of from 200 to 700 nm at a content of 25 mass % or more, and inorganic particles (B2) each having a particle diameter of from 40 to 100 nm at a content of 10 mass % or more,
by applying a shear flow field and an elongation field, wherein a volume ratio of the inorganic particles (B1) with respect to a total volume of the inorganic particles (B1) and the inorganic particles (B2) is from 0.6 to 0.8.

8. A manufacturing method for an organic/inorganic composite, comprising:
supplying raw materials including
(A) 100 parts by mass of a thermoplastic resin containing as a main component at least one kind selected from a polyarylketone resin and a polysulfone resin, and (B) 60 to 300 parts by mass of an inorganic particle mixture containing inorganic particles (B1) each having a particle diameter of from 200 to 700 nm at a content of 25 mass % or more, and inorganic particles (B2) each having a particle diameter of from 40 to 100 nm at a content of 10 mass % or more, to a melt-kneading apparatus including an internal-return screw that transfers a melt-kneaded product of the raw materials, which is transferred to a screw forward end, back to a rear end; and melt-kneading the raw materials under heating at from 200 to 500° C. under conditions of a rotation number of the screw of from 300 to 3,000 rpm and a shear rate of from 450 to 4,500 sec-1 by circulating the raw materials for a given period of time, wherein a volume ratio of the inorganic particles (B1) with respect to a total volume of the inorganic particles (B1) and the inorganic particles (B2) is from 0.6 to 0.8.

9. The manufacturing method for an organic/inorganic composite according to claim 7, wherein (B) the inorganic particle mixture comprises inorganic particles surface-treated with a surface treatment agent containing a (meth)acrylic group.

10. The manufacturing method for an organic/inorganic composite according to claim 9, wherein the inorganic particles surface-treated with a surface treatment agent containing a (meth)acrylic group comprise inorganic particles surface-treated with a surface treatment agent represented by the following formula (1):

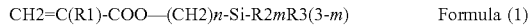

CH2=C(R1)-COO—(CH2)$n$-Si-R2$m$R3(3-$m$)   Formula (1)

in the formula (1), R1 represents a hydrogen atom or a methyl group, R2 represents an alkoxy group having 1 to 6 carbon atoms, an isocyanate group, or a chlorine atom, R3 represents a hydrocarbon group having 1 to 6 carbon atoms, m represents 1, 2, or 3, and n represents an integer of from 3 to 20.

11. A dental material, comprising a organic/inorganic composite, wherein the organic/inorganic composite comprise:
(A) 100 parts by mass of a thermoplastic resin containing as a main component at least one kind selected from a polyarylketone resin and a polysulfone resin; and
(B) 60 to 300 parts by mass of an inorganic particle mixture dispersed in the thermoplastic resin,
wherein the inorganic particle mixture contains inorganic particles (B1) each having a particle diameter of from 200 to 700 nm at a content of 25 vol % or more, and inorganic particles (B2) each having a particle diameter of from 40 to 100 nm at a content of 10 vol % or more, and
wherein a volume ratio of the inorganic particles (B1) with respect to a total volume of the inorganic particles (B1) and the inorganic particles (B2) is from 0.6 to 0.8.

12. A bone substitute material, comprising a organic/inorganic composite, wherein the organic/inorganic composite comprise:
(A) 100 parts by mass of a thermoplastic resin containing as a main component at least one kind selected from a polyarylketone resin and a polysulfone resin; and
(B) 60 to 300 parts by mass of an inorganic particle mixture dispersed in the thermoplastic resin,
wherein the inorganic particle mixture contains inorganic particles (B1) each having a particle diameter of from 200 to 700 nm at a content of 25 vol % or more, and inorganic particles (B2) each having a particle diameter of from 40 to 100 nm at a content of 10 vol % or more, and
wherein a volume ratio of the inorganic particles (B1) with respect to a total volume of the inorganic particles (B1) and the inorganic particles (B2) is from 0.6 to 0.8.

13. The manufacturing method for an organic/inorganic composite according to claim 8, wherein (B) the inorganic particle mixture comprises inorganic particles surface-treated with a surface treatment agent containing a (meth)acrylic group.

14. The manufacturing method for an organic/inorganic composite according to claim 13, wherein the inorganic particles surface-treated with a surface treatment agent containing a (meth)acrylic group comprise inorganic particles surface-treated with a surface treatment agent represented by the following formula (1):

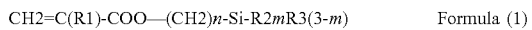

CH2=C(R1)-COO—(CH2)$n$-Si-R2$m$R3(3-$m$)   Formula (1)

in the formula (1), R1 represents a hydrogen atom or a methyl group, R2 represents an alkoxy group having 1 to 6 carbon atoms, an isocyanate group, or a chlorine atom, R3 represents a hydrocarbon group having 1 to 6 carbon atoms, m represents 1, 2, or 3, and n represents an integer of from 3 to 20.

15. The organic/inorganic composite according to claim 1, wherein the volume ratio of the inorganic particles (B1) with respect to the total volume of the inorganic particles (B1) and the inorganic particles (B2) is from 0.7 to 0.8.

16. The manufacturing method for an organic/inorganic composite according to claim 7, wherein the volume ratio of the inorganic particles (B1) with respect to the total volume of the inorganic particles (B1) and the inorganic particles (B2) is from 0.7 to 0.8.

17. The manufacturing method for an organic/inorganic composite according to claim 8, wherein the volume ratio of the inorganic particles (B1) with respect to the total volume of the inorganic particles (B1) and the inorganic particles (B2) is from 0.7 to 0.8.

18. The dental material according to claim 11, wherein the volume ratio of the inorganic particles (B1) with respect to the total volume of the inorganic particles (B1) and the inorganic particles (B2) is from 0.7 to 0.8.

19. The bone substitute material according to claim 12, wherein the volume ratio of the inorganic particles (B1) with respect to the total volume of the inorganic particles (B1) and the inorganic particles (B2) is from 0.7 to 0.8.

* * * * *